United States Patent
Lipman

(10) Patent No.: US 7,335,416 B2
(45) Date of Patent: Feb. 26, 2008

(54) MOULDABLE HYDROCOLLOID ADHESIVE COMPOSITIONS

(75) Inventor: Roger D. A. Lipman, Turnhout (BE)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/473,959

(22) PCT Filed: Apr. 17, 2002

(86) PCT No.: PCT/GB02/01766

§ 371 (c)(1),
(2), (4) Date: Sep. 30, 2003

(87) PCT Pub. No.: WO02/087646

PCT Pub. Date: Nov. 7, 2002

(65) Prior Publication Data

US 2004/0109885 A1    Jun. 10, 2004

(30) Foreign Application Priority Data

Apr. 26, 2001    (GB) ................... 0110284.7

(51) Int. Cl.
*C09J 121/00*    (2006.01)
(52) U.S. Cl. .............. 428/343; 524/35; 524/37; 524/71; 524/274; 523/111; 523/118
(58) Field of Classification Search ........ 428/343; 524/35, 37, 71, 274; 523/111, 118
See application file for complete search history.

(56) References Cited

U.S. PATENT DOCUMENTS

| | | | |
|---|---|---|---|
| 3,281,383 A | 10/1966 | Zelinski et al. | |
| 4,166,051 A | 8/1979 | Cilento et al. | |
| 4,204,540 A | 5/1980 | Cilento et al. | |
| 4,350,785 A | 9/1982 | Habib | |
| 4,393,080 A * | 7/1983 | Pawelchak et al. | 428/355 R |
| 4,505,976 A * | 3/1985 | Doehnert et al. | 428/355 CP |
| 4,551,490 A | 11/1985 | Doyle et al. | |
| 5,274,036 A | 12/1993 | Korpman et al. | |
| 5,492,943 A | 2/1996 | Stempel | |
| 5,622,711 A | 4/1997 | Chen | |
| 5,827,528 A | 10/1998 | Kubo et al. | |
| 5,916,959 A * | 6/1999 | Lindquist et al. | 524/505 |
| 6,375,977 B1 | 4/2002 | Auguste et al. | |

FOREIGN PATENT DOCUMENTS

| | | |
|---|---|---|
| EP | 0 048 556 A1 | 3/1982 |
| EP | 0 651 983 B1 | 5/1995 |
| EP | 0 730 874 A2 | 9/1996 |
| FR | 2 775 903 A1 | 9/1999 |
| GB | 1 430 515 | 3/1976 |
| GB | 2 259 464 A | 3/1993 |
| WO | WO 98/17329 | 4/1998 |
| WO | WO 98/53771 | 12/1998 |
| WO | WO 98/54268 | 12/1998 |
| WO | WO 99/11728 | 3/1999 |
| WO | WO 00/53690 | 9/2000 |

OTHER PUBLICATIONS

"Hydrocolliod PSAs; New Formulations and Strategies" by Lipman., Medical Device and Diagnostic Industry, 1999, pp. 132-148.*
International Search Report of PCT/GB02/01766, dated Aug. 14, 2002.
International Preliminary Examination Report of PCT/GB02/01766, dated Mar. 5, 2003.

* cited by examiner

*Primary Examiner*—Irina S Zemel
(74) *Attorney, Agent, or Firm*—Christie, Parker & Hale, LLP.

(57) ABSTRACT

A mouldable pressure-sensitive hydrocolloid adhesive composition, particularly useful as a medical adhesive, comprising a dispersion of a discontinuous phase of one or more water-soluble and/or water swellable absorbent polymers in a continuous phase comprising a thermoplastic elastomer, a compatible liquid rubber, a polyisobutylene and a low-molecular weight polybutene.

9 Claims, 2 Drawing Sheets

MOULDABLE HYDROCOLLOID ADHESIVE COMPOSITIONS

CROSS-REFERENCE TO RELATED APPLICATION

This application is a National Phase Patent Application of International Application No. PCT/GB02/01766, filed on Apr. 17, 2002, which claims priority of British Patent Application No. 0110284.7, filed on Apr. 26, 2001.

Hydrocolloid pressure sensitive adhesives are comprised of dispersions of fluid absorbent materials in pressure sensitive adhesive matrices. These adhesives are well known in medical fields where they find use as multifunctional components of medical devices. In particular, hydrocolloid adhesives have been extensively utilised in the fields of ostomy care and wound care. In ostomy care, hydrocolloid adhesives are used as the barrier adhesive to hold the pouch in place on the peristomal skin, and to protect this skin from the excoriating effects of body waste. In wound care, hydrocolloid adhesives have been used as the basis of absorbent dressings for direct application to especially chronic wounds.

Hydrocolloid compositions are normally not very flexible or conformable, so that adhesion to movable and curved body parts is difficult. This lack of flexibility can give rise to problems. For example, an ostomy patient with folded or scarred skin in the region of his stoma may have difficulty in adhering the hydrocolloid adhesive of his pouch to the peristomal skin without getting a leak between the skin and the adhesive. Leaks would allow highly irritating and excoriating faeces or urine to come into contact with the skin. The present invention is directed at new hydrocolloid adhesives that overcome some of these problems of the prior art adhesives, and extend the utility of hydrocolloid adhesives into new application areas. Specifically, this invention is directed at hydrocolloid adhesives that are mouldable, and that can be readily adapted to curved and movable body parts.

The prior art discloses products designed to overcome the shortcomings of inflexible hydrocolloid skin barriers. In the field of ostomy care, adjunct products such as ostomy paste are well known. Such products are useful for protecting and treating the skin contiguous to a stoma. The problem of fluid leakage is often aggravated where the skin around the stoma is irregular, or where folds of skin occur in this area. To obtain an improved seal the ostomate can apply a coating of paste in a ring around the stoma, allow the paste to dry, and then apply the ostomy pouch over the dried paste.

A number of ostomy paste compositions appear in the prior art. For example, British Patent Specification 1,430,515 to Hollister, Inc., U.S. Pat. No. 4,350,785 to Hollister Inc. and European Patent Application 0048556 A1 to E. R. Squibb & Sons, all describe combinations of film forming polymers with water absorbable hydrocolloid powders to form a paste which is dispensable from a tube. The problem with these compositions is that they have to have a viscosity low enough for the user to squeeze them from the tubes and therefore they contain a solvent, usually an alcohol such as isopropanol or ethanol, which can sting the skin on application. Also, often the preparation can harden in the tube, and become difficult or impossible to apply.

U.S. Pat. Nos. 4,166,051 and 4,204,540 suggest an alternative approach to the problem of securing an inflexible ostomy pouch barrier around the stoma of an ostomy patient with an irregular skin surface. These two patents are directed to homogeneous compositions of a pressure sensitive adhesive component, mineral oil, hydrocolloid gums and cohesive strengthening agents, optionally with added elastomers such as butyl rubber or medium molecular weight polyisobutylene. The putty-like compositions can be shaped so as to fill the area between the stoma and the skin barrier. The compositions can be employed to smooth an area of the abdomen around the stoma so as to provide a relatively flat surface to which an appliance or skin barrier can be securely attached. They have the advantage over ostomy paste in that they do not contain alcohol, and hence do not sting the skin upon application.

PCT International Application WO 98/17329 to Coloplast discloses a mouldable mass of a putty-like adhesive for use in connection with an ostomy appliance. The composition comprises 1-20 wt % of a block copolymer having a major content of di-block copolymer, 5-60 wt % of a tackifying liquid constituent and 1-10 wt % of a waxy constituent. The product can be extruded and slit into a rod form that can then be packed into blisters. The rods can be protected with silicone release paper. Even though the composition is said to be removable from the skin as an integrated unit, without leaving residues, the composition suffers from the drawback of being very sticky, and difficult to use because of its tackiness.

Eakin Cohesive, a hydrocolloid product available from T. G. Eakin & Sons, Comber, Northern Ireland, is said to be a mouldable, easily shaped, moisture absorbing skin barrier. According to information extracted from the Eakin website, http://www.eakin.co.uk, it can be stretched, compressed and moulded to fit the exact shape and size as required. Eakin Cohesive contains no active ingredients but is said to contain a unique carbohydrate which is slowly released while the seal is in place, diluting harmful enzymes, and protecting the skin against body wastes and fluids such as bile and ileal fluid. The product can be used as a seal under stoma pouches and appliances, as a packing agent in skin folds and scars, as a seal around drain tubes and fistulae, and as a "picture frame" around wound edges prior to dressing application. Eakin Cohesive is, however, not recommended for use in open wounds.

Eakin Cohesive is functionally comparable to ostomy pastes in that both products can be moulded and formed to fill up scar areas and help to produce a flat skin surface. However, although Eakin Cohesive Seals and ostomy pastes perform the same or similar functions, there are fundamental differences in their performance. Patient studies revealed that Cohesive Seals are easier to store, handle, mould, apply and remove from the skin. In general they were quicker and easier to use than the ostomy pastes and patients felt more comfortable and confident when wearing them. Average pouch wear time was increased with use of the Eakin Cohesive.

In comparison, the ostomy pastes were found to be messy to use, left a residue on the skin, and were uncomfortable to remove. Ostomy pastes were also noticeably less effective at improving the condition of red or excoriated skin.

These patient studies show that a mouldable adhesive or putty such as the Cohesive product is a better solution than is ostomy paste to the problem of uneven skin in the peristomal area. Notwithstanding these advantages, however, there are several drawbacks with the Eakin Cohesive product. It preferably has to be warmed to body temperature before use. If the seal is not warmed, it may appear to "crumble" and will be more difficult to mould. Cohesive is not an integrated hydrocolloid. This means that in the presence of body fluid such as faeces, urine or wound exudate, the composition breaks down to give a soft gel and becomes amorphous as it gets saturated with fluid. It is therefore an objective of the present invention to make an improved mouldable hydrocolloid for ostomy care.

Eakin Cohesive cannot be used in direct contact with wounds. A mouldable hydrocolloid adhesive that could be used in the presence of exuding wounds would find utility as a wound packing, and provide a means of extending the duration of wear of conventional hydrocolloid dressings, especially in the presence of wound exudate.

European Patent EP 0 651 983 B1 discloses a trimmable wound dressing in which a spiral of hydrocolloid is unwound to make a rope of rectangular cross section which can be used to pack a wound. The compositions contain about 20 wt % elastomer and are elastic and not mouldable. On the contrary, they are said to retain their shape in use. Such a structure will expand in the wound as it absorbs wound exudate and, because of its relatively high elastic modulus, may exert considerable pressure on the wound bed.

It is therefore a further objective of the present invention to make a mouldable hydrocolloid that is suitable for direct contact with wounds, and that will readily conform to wound cavities.

Ostomates who have a retracted stoma, or whose stoma is difficult to pouch because it is hidden by folds of skin, can have additional problems with leaky appliances. In order to help to deal with this problem, pouches with convex faceplates have been developed. The convex faceplate, especially when pressed around the stoma by means of a belt worn around the body and attached to either side of the pouch adhesive flange, causes the retracted stoma to protrude further into the pouch, thus reducing the propensity for pouch leakage. The use of convex faceplates in the design of ostomy pouches is becoming more common, and the markets for them are growing. The manufacture of convex ostomy products would be facilitated with the use of mouldable hydrocolloids, which can be formed around a plastic convex plate under the influence of heat and pressure. It is therefore still a further objective of the present invention to formulate a hydrocolloid adhesive that is suitable for fabrication into an ostomy barrier having a convex faceplate.

BRIEF DESCRIPTION OF THE DRAWINGS

The invention will be better understood when considered in light of the following detailed description and the appended drawings, wherein.

Figure 1:
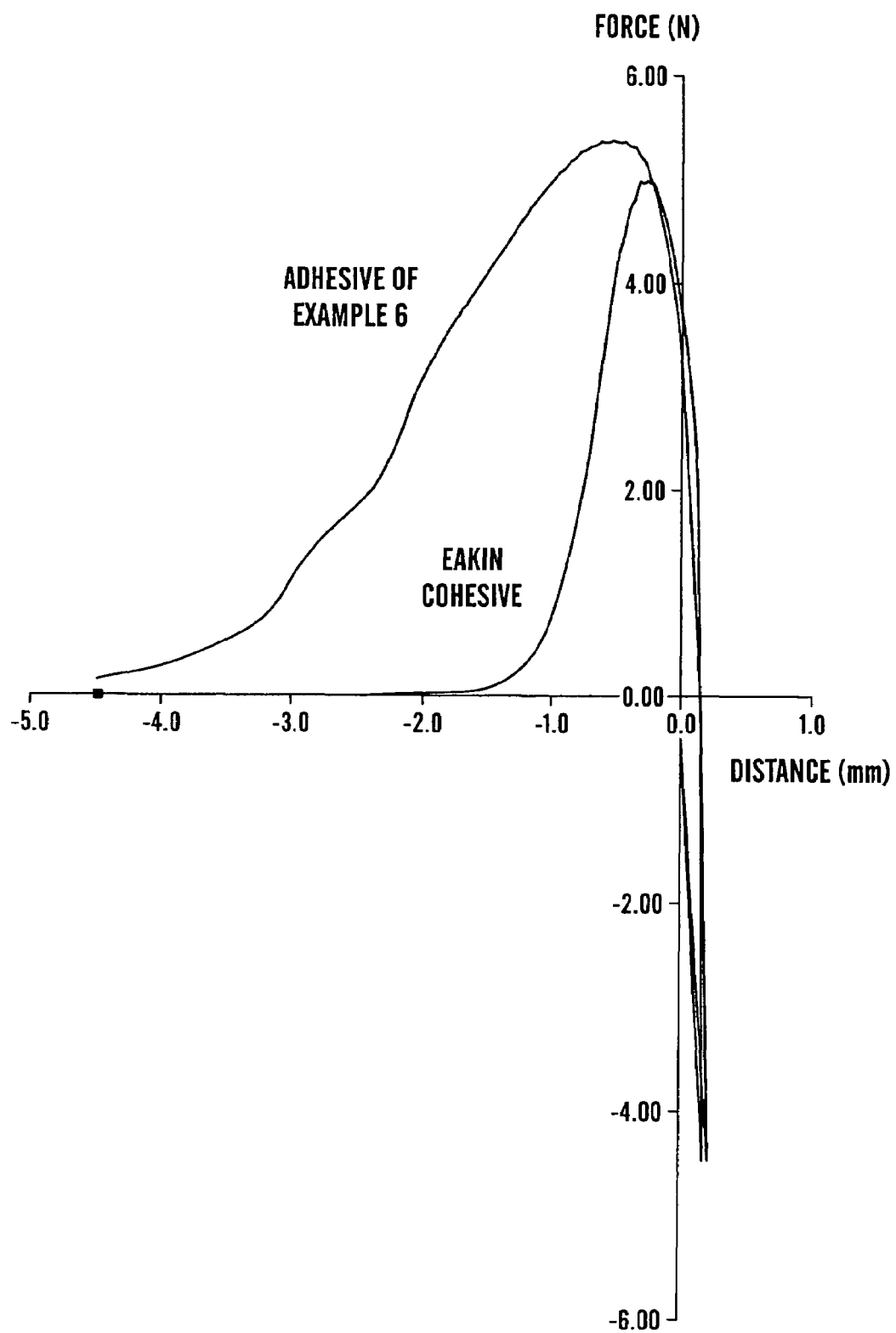
FIG. 1 is a graphical comparison of the penetration test performance of (a) a mouldable hydrocolloid adhesive corresponding to one embodiment of the invention (Ex. 6) and (b) a known product (Eakin Cohesive)

We have found very unexpectedly that hydrocolloid compositions containing small amounts of thermoplastic elastomer, and tackified with liquid rubbers for example as disclosed in U.S. Pat. No. 5,274,036, provide the basis for mouldable compositions more mouldable than Eakin Cohesive and that show no inclination to crumble at room temperature. Some of these compositions are moreover very highly integrated. Specific embodiments of the invention can be used in direct contact with open wounds to provide mouldable compositions useful for wound packing that allow versatile management of such wounds.

A mouldable composition according to the invention comprises a continuous phase containing a mixture of a permanently tacky pressure sensitive adhesive, preferably a holt melt adhesive based on a styrene-containing thermoplastic clastomer and a liquid rubber, a low molecular weight polyisobutylene and a low molecular weight liquid polybutene, and dispersed within the continuous phase a discontinuous phase of one or more water soluble and/or water swellable absorbent polymers.

Suitable styrene-containing thermoplastic elastomers useful in the practise of this invention include block copolymers based on styrene-butadiene, styrene-isoprene or styrene ethylene-butylene. Also, a low styrene synthetic copolymer of butadiene and styrene, commonly called SBR rubber, can be used as the thermoplastic elastomer. The elastomer may consist of linear or radial A-B-A block copolymers or mixtures of these A-B-A copolymers with simple A-B block copolymers. However, the proportion of A-B block copolymers in the mixture of A-B-A and A-B block copolymers should not exceed about 85% by weight and lower percentages would normally be used.

The A-B-A block copolymers are of the type which consist of A blocks derived from styrene or one of its homologues and B blocks derived from conjugated dienes, such as butadiene or isoprene, or from lower alkenes such as ethylene or butylene. The radial A-B-A polymers useful in this invention are of the type described for example in U.S. Pat. No. 3,281,383 and conform to the general formula $(A-B)_nX$, where A and B comprise blocks derived from monomers described above in connection with the A-B-A copolymers, X is an organic or inorganic connecting moiety having a functionality of at least 2, and n is equal to the functionality of X. The A-B block copolymers useful in this invention comprise A and B blocks derived from monomers described above in connection with the A-B-A copolymers.

Liquid rubbers useful in this invention are synthetic liquid isoprene rubber, depolymerised natural rubber, carboxyl terminated synthetic liquid isoprene-styrene rubber, hydroxyl terminated synthetic liquid isoprene rubber, hydrogentated liquid isoprene rubber, liquid isoprene-styrene copolymer, liquid isoprene-butadience copolymer and liquid butadiene-styrene copolymer. The liquid rubbers have a molecular weight of about 25,000 to about 50,000. Preferably, the liquid rubbers have a glass transition temperature of less than −50° C., and a melt viscosity at 38° C. of from 500-10,000 poises. It will be appreciated that other liquid rubbers known in the art could be useful in the present invention.

The polyisobutylene component is exemplified by the Vistanex LM series of polyisobutylenes, available from Exxon Chemical Corporation, and which have Flory viscosity average molecular weights in the range 35,000 to 70,000, and Brookfield viscosities at 175° C. within the range 20,000 and 140,000 mPa.s.

The low molecular weight polybutene components are exemplified by the Hyvis series of materials from BP, and by the Parapol series of products from Exxon Chemical Corporation, and which have molecular weights ranging from 1000 to 3000, determined using test method AM-I 841-86, and kinematic viscosities at 100° C. within the range 180 and 3500 cSt, as measured by test method ASTM D445.

Normally a suitable processing stabiliser would also be included in the hot melt adhesive component. Suitable stabilisers useful in the practise of the invention include those indicated for use with styrene-olef in styrene block copolymer thermoplastic elastomers such as organophosphites and the so-called hindered phenols, but any suitable stabilisers may be employed. An example of an organophosphite stabiliser is tris(nonylphenyl) phosphite, available as Polygard HR manufactured by Uniroyal. Particularly useful are the hindered phenols, Irganox 1010 and Irganox 565, manufactured by Ciba. Irganox 1010 is pentaerythritol tetrakis (3-(3, 5-di-tert-butyl-4-hydroxyphenyl)propionate. Irganox 565 is 2, 6-di-tert-butyl-4-(4,6-bis(octylthio)-1, 3,5-triazin-2- ylamino)phenol. Stabilisers may be us or in combination, and suitable ranges are from 0.3 1.5% by weight based on the total formulation. The stabilisers are always added to the continuous phase, as is shown in the examples.

Other optional ingredients such as tackifiers and plasticisers may be added to the continuous phase, to modify tack and optimise adhesion properties.

The hot melt adhesive component is comprised of the thermoplastic elastomer and the liquid rubber, both as defined above, and is substantially resin free. Preferably this hot melt adhesive is formed with a weight ratio of thermoplastic elastomer to liquid rubber of about 1:0.5 to about 1:7. The amount of liquid rubber used is varied for the desired degree of adhesiveness and tackiness of the pressure sensitive adhesive The amount of hot melt adhesive used in the compositions is such that mouldability is not compromised. The composition should preferably contain at least 1 wt. % of this component but if too much thermoplastic elastomer is present in the formulation, the compositions will be too elastic to function as a mouldable material. The preferred upper limit of thermoplastic elastomer in the formulation is 5 wt %, more preferably 3 wt % and most preferably 2 wt %. In addition, the amount of liquid rubber is also important, and a maximum amount of liquid rubber emanating from the intermediate hot melt adhesive corresponding to 10 wt % of the total formulation is permitted. Preferably, the maximum amount of liquid rubber is limited to 8 wt % of the total formulation.

The polyisobutylene component may be present in an amount from 25 wt % to 45 wt % of the total formulation, preferably from 30 wt % to 40 wt % of the total formulation.

The low molecular weight polybutene may be present in an amount from 5 wt % to 20 wt % of the total formulation, and preferably from 7 wt % to 15 wt %.

The discontinuous phase comprises one or more hydrophilic polymers that are soluble or insoluble but swellable in water as the moisture-absorbing component. One or more swellable polymers may be present. Suitable insoluble swellable polymers include cross-linked sodium carboxymethyl cellulose, crystalline sodium carboxymethyl cellulose, cross-linked dextran and starch-acrylonitrile graft copolymer. The swellable polymer may also be a so- called "super absorbent" material such as starch sodium polyacrylate. Other hydratable polymers such as gluten and polymers of methyl vinyl ether and maleic acid and derivatives thereof may also be included in the discontinuous phase. Suitable water soluble polymers include sodium carboxymethyl cellulose, pectin, gelatIne, guar gum, locust bean gum, collagen, karaya gum and starch, particularly maize starch, and the like. The discontinuous phase should not normally exceed 60% of the total weight of the adhesive, preferably does not exceed 55% by weight of the adhesive, and more preferably does not exceed 50% by weight of the adhesive, and may be comprised of any combination of soluble and/or insoluble absorbents.

Optional fillers such as silica and pigments and optional active ingredients such as antimicrobial compounds may also be incorporated into the compositions of the invention. Silver sulfadiazine and benzalkonium chloride represent non-limiting examples of such antimicrobial ingredients.

The adhesive compositions of the invention may be prepared as follows. The thermoplastic elastomer and the liquid rubber component are blended together in a suitable mixer, normally a sigma blade mixer with an extruder discharge. The mixer is heated to about 170° C. A nitrogen flow of about 60 ml/sec through the mixer reduces the possibility of oxidative degradation of the rubber during processing. About 1% phr of a suitable stabiliser, such as Irganox 1010 available from Ciba-Geigy, can be added at this stage. The thermoplastic elastomer is allowed first to blend in the mixer until it coalesces. Normally a small amount of the liquid rubber, for example, 10-20% to the whole amount of the thermoplastic elastomer and the liquid rubber is allowed to blend with the softened thermoplastic elastomer. When all this 10-20% of the liquid rubber has been absorbed, another portion of the liquid rubber is added, for example, 20-30%, and the liquid rubber is absorbed into the styrene-olefin-styrene rubber. This is continued until all the liquid rubber is added, when a pourable tacky intermediate adhesive is obtained. The mixer blades are stopped, the direction of the screw is reversed, and the intermediate adhesive is removed from the mixer. It is run off into suitable release coated containers and allowed to cool.

The mixer is cleaned, stabilised at 90° C. and the powdery hydrocolloid ingredients are charged to the mixer together with the polyisobutylene. These are blended until uniform for about 10 minutes and then the previously blended hot melt adhesive component is added and the mixer temperature is raised to 105° C. After mixing at 105° C. for 15 min the temperature of the mixer is dropped to about 80° C. and the low molecular weight polybutene is added. Mixing is continued normally for a further 20 minutes or so. The fully mixed mass is then removed from the mixer. It can then be extruded or pressed to the desired thickness, laminated to suitable substrates and die cut to shapes if needed.

The above manufacturing process has been described with respect to a two-step process in which the hot melt adhesive comprising the styrene-containing thermoplastic elastomer and the liquid rubber and the stabiliser is first manufactured and isolated and which is then subsequently used to make the compositions of the invention. It will be appreciated by anyone skilled in the art that no process limitation is implied and the adhesives of the invention may equally well be prepared in a one-pot process, with no isolation of the intermediate hot melt adhesive.

The following test methods were used to characterise the products.

Static Absorption of Hydrocolloids

To determine the amount of fluid uptake into a known surface area of hydrocolloid adhesive.

Procedure

Cups with flanges for use in determination of Moisture Vapour Transmission are suitable for use in this test. Laminate release liner to the upper flange of the cup with the double coated tape. This is the contact zone for the hydrocolloid. Fill the cup with 30 ml NaCl solution (0.9% wt). Cut a sample of hydrocolloid of about the same size as the outer cup diameter. Weigh the sample ($W_1$). Laminate the sample to the cup, making sure that the seal between the hydrocolloid sample and the cup is water tight. Turn the cup upside down and put it in the oven at 37° C. for 24 hours. Cool down. Remove the hydrocolloid from the cup and reweigh ($W_2$). Calculate the water fluid absorption (g/sq. m. 24 h) using the formula:

$$absorption = (W_2 - W_1)/0.002375$$

where the area of the hydrocolloid in contact with salt solution is 0.002375 sq. m.

Determination of the Integrity

The integrity of a hydrocolloid is defined as its ability to resist breakdown by biological fluids. The test measures the weight percentage of hydrocolloid retained after exposure to saline under specified conditions.

Procedure

Condition the hydrocolloid samples at 23±1° C. and 50±2% relative humidity for 24 hours. Cut circular samples from the hydrocolloid sheet 2.54 cm diameter. Weigh and record the samples ($W_i$). Place each sample in a 120 ml (4 oz) bottles with screw caps (Vel Catalog Number 1198017) with 50 ml physiological saline (NaCl 0.9% wt in water), cap the bottles and agitate on a bottle shaker at maximum speed for a period of 18 hrs. Remove the samples and dry them in a circulating air oven at 50° C. and 50% relative humidity until dry. This usually takes about 24 hours. Reweigh the sample ($W_f$). The Integrity Value of the sample is calculated using the following equation:

$$\text{Integrity Value}(\%) = 100 \times \frac{(W_f)}{(W_i)}$$

Note: The test may be run with hydrocolloid with or without carrier. However, the result may be affected, and suitable control samples should always be included.

Determination of Mouldability

Assessment of the mouldability of the hydrocolloid materials was made using the test methods described in Adhesives Age, September 1997, pp 18-23. The equipment used was a probe tester manufactured by Stable Micro Systems, Godalming, Surrey, England, driven by custom designed software.

Using the equipment, the energy absorbed by the mouldable adhesive as the probe penetrated the adhesive was determined by a transducer. The probe is moved up and down by a rotating screw which is driven by a stepping motor. The displacement of the probe was measured through the motor rotation.

For each measurement, the probe was a stainless steel ball of 25.4 mm in diameter. The compressive force was 4.5N and the test speed was 0.04 mm/sec.

The raw materials used in the examples are as follows:
Escorez 2203LC—Exxon Chemical—Tackifying resin
Regalite 1100—Hercules Chemical—" "
Adtac LV-E—Hercules Chemical—" "
LVSI-101—Kraton Polymers—Liquid rubber
Vector 4111—Exxon Chemical—Thermoplastic elastomer
Kraton D-1161NS—Kraton Polymers—" "
Irganox 1010—Ciba Chemicals—Antioxidant
Parapol 1300—Exxon Chemical—Polybutene
Vistanex LMMS—Exxon Chemical—Polyisobutylene
Maize Starch—National Starch and Chemical
Pectin USP100—Hercules Chemical
Blanose 7H4XF—Hercules Chemical—Sodium carboxymethyl cellulose
Aquasorb A500—Hercules Chemical—Sodium carboxymethyl cellulose
Kaydol Mineral Oil—Witco Chemical The invention will now be further described with reference to the following non-limiting examples. While Examples 6 through 12 illustrate the application of the present invention to constructions generally suitable for use in ostomy care, and Examples 13 through 27 show formulations generally more suitable for use in wound care applications, it will be understood that no limitation is implied by this separation.

EXAMPLE 1

This example illustrates preparation of the intermediate hot melt adhesive.

|  | wt % total | Amount, gm |
| --- | --- | --- |
| LVSI-101 | 79.37 | 400 |
| Kraton KD-1161N | 19.84 | 100 |
| Irganox 1010 | 0.79 | 4 |
|  | 100.00 | 504 |

A Z-blade mixer of 1 kg. capacity was purged with nitrogen gas and heated to 160° C. The speed of the front, faster, blade was 30 rpm. The Kraton KD-1161N and the Irganox 1010 were charged to the Mixer at 160° C., and the mixer was started. After mixing for 5 minutes, the rubbery crumb coalesed, and 50 gm of the LVSI-101 was added with continued mixing and nitrogen purging. After a further ten minutes, the temperature was raised to 170° C. and the mixer front blade speed increased to 47 rpm. The LVSI had at this point completely mixed with the rubber, and a further 51 gm of LVSI was added. Ten minutes later, after blending of the second portion of the LVSI, a further 48 gm of LVSI was added, and mixed for a further 10 minutes. In this way, approximately 50 gm portions of the charge of LVSI were added every 10 minutes until all the 400 gm had been added. 15 minutes later, the intermediate adhesive was dumped from the mixer. The total time for this operation was about 90 minutes.

EXAMPLE 2

In a similar way to Example 1, the following adhesive was made.

|  | wt % total | Amount, gm |
| --- | --- | --- |
| LVSI-101 | 59.54 | 300 |
| Kraton KD-1161N | 39.68 | 200 |
| Irganox 1010 | 0.80 | 4 |
|  | 100.02 | 504 |

EXAMPLE 3

This example illustrates the preparation of a more conventional hot melt adhesive used in the formulations. The mixer was purged with nitrogen gas and heated to 160° C. The Regalite R1100, 200 gm. and the Irganox 1010 were charged to the mixer at 160° C., and warmed for 15 minutes.

The amount of Vector 4111 triblock S-I-S elastomer from Exxon Chemical was added. After mixing for 70 minutes, the remainder of the Regalite and the Adtac LV-E were added over 35 minutes. The adhesive was run off from the mixer into release coated containers and cooled.

|  | wt % total | Amount, gm |
|---|---|---|
| Regalite R1100 | 45.08 | 362 |
| Irganox 1010 | 0.75 | 6 |
| Vector 4111 | 36.11 | 290 |
| Adtac LV-E | 18.06 | 145 |
|  | 100.0 | 803 |

EXAMPLE 4-5

In an analogous fashion to Example 3, two further intermediate adhesives were prepared having the following compositions:

|  | wt % total | Amount, gm |
|---|---|---|
| Example 4 |  |  |
| Escorez 2203 LC | 41.69 | 336 |
| Irganox 1010 | 0.74 | 6 |
| Kraton D-1161NS | 37.72 | 304 |
| Adtac LV-E | 19.85 | 160 |
|  | 100.0 | 806 |
| Example 5 |  |  |
| Regalite R1100 | 46.12 | 320.0 |
| Irganox 1010 | 2.39 | 16.6 |
| Kraton D-1161NS | 33.04 | 229.2 |
| Mineral Oil | 18.45 | 128.0 |
|  | 100.0 | 693.8 |

EXAMPLE 6

This example illustrates the manufacture of a mouldable hydrocolloid formulation suitable for use by ostomy patients as a filler for uneven skin under an ostomy pouch, and for conversion to a convex faceplate pouch barrier construction.

Maize Starch (96 gm), Pectin USP100 (40 gm) and sodium carboxymethyl cellulose, Blanose 7H4XF (100 gm) were charged to a laboratory scale 1l. Z-blade mixer, previously heated to 90° C. After blending the powders for 2 minutes, Vistanex LMMS polyisobutylene (164 gm) was added, and mixing was continued for 10 minutes, at the end of which time the temperature of the mixer was raised to 105° C. The hot melt adhesive 2-18A from Example 1 (40 gm) was added to the mixer, and blending was continued for a further 10 minutes, at the end of which time the temperature in the mixer was dropped to 85° C. Parapol 1300 (40 gm) was added gradually to the contents of the mixer and kneading was continued for 20 minutes after the final addition of the Parapol ingredient. The mixer was stopped and the hydrocolloid was removed. It was extruded in a laboratory extruder between two silicone coated release papers to a web of 2.4 mm thickness.

The mouldable hydrocolloid was evaluated and found to have an absorbency of 7742 Gms/sq. m./24 hrs, and an integrity of 93.8%. The results are shown in TABLE 1.

EXAMPLES 7-10

In an analogous fashion to Example 6, mouldable hydrocolloids of Examples 7-10 were made and evaluated, with the results shown in the TABLE 1 below.

TABLE 1

|  | Formulation, wt % | | | | |
|---|---|---|---|---|---|
|  | Ex. 6 | Ex. 7 | Ex. 8 | Ex. 9 | Ex. 10 |
| Hot Melt of Example | 1 | 2 | 3 | 5 | 4 |
| LVSI-101 | 6.61 | 4.96 | — | — | — |
| Kraton D-1161NS | 1.65 | 3.31 | — | 2.75 | 3.14 |
| Vector 4111 | — | — | 3.01 | — | — |
| Irganox 1010 | 0.07 | 0.07 | 0.06 | 0.20 | 0.06 |
| Regalite 1100 | — | — | 3.76 | 3.84 | — |
| Adtac LV-E | — | — | 1.50 | — | 1.65 |
| Mineral Oil | — | — | — | 1.54 | — |
| Escorez 2203 LC | — | — | — | — | 3.47 |
| Vistanex LMMS | 34.17 | 34.17 | 34.17 | 34.17 | 34.17 |
| Pectin USP100 | 8.33 | 8.33 | 8.33 | 8.33 | 8.33 |
| Blanose 7H4XF | 20.83 | 20.83 | 20.83 | 20.83 | 20.83 |
| Maize Starch | 20.00 | 20.00 | 20.00 | 20.00 | 20.00 |
| Parapol 1300 | 8.33 | 8.33 | 8.33 | 8.33 | 8.33 |
| Properties |  |  |  |  |  |
| Liquid rubber: Thermoplastic elastomer, wt/wt | 4.00 | 1.50 | (1.75) | (1.40) | (1.86) |
| Static Absorption Gms/sq. m./ 24 hrs | 7742 | 6379 | 8295 | 7061 | 8290 |
| Integrity, % | 94 | 12 | 20 | 10 | 10 |
| Thickness, mm | 2.4 |  | 2.0 | 2.0 | 2.0 |

The results from TABLE 1 are striking and show the surprising result that, at the low level of rubber used, only the one intermediate hot melt adhesive used in Example 6 serves to integrate the hydrocolloid. Example 7 contains a higher amount of S-I-S thermoplastic elastomer, and a higher thermoplastic elastomer:liquid rubber ratio than does the adhesive of Example 6. The mouldable adhesives from comparative examples 8, 9 and 10, which have no liquid rubbers, but rather contain conventional tackifying agents, have very little integrity. The data show that, in the adhesive system exemplified by Example 6, an upper rubber concentration limit of 2% by weight, and a thermoplastic elastomer: liquid rubber ratio of less than 1:1.5, and preferably 1:4, appears necessary to get integration.

EXAMPLE 11

The mouldable hydrocolloid from Example 6 was compared with the Eakin Cohesive product. The data on each are given in TABLE 2. It can be clearly seen that the integrity of the Eakin product is close to zero (the 10% integrity measured actually derives from the residual plastic film that was laminated to the product for the test). Typical penetration data are shown in the curves of FIG. 1. It can very clearly be seen that the energy absorbed by the hydrocolloid of Example 6 is far greater than that of the comparatively rigid Eakin Cohesive product, demonstrating the softness and easier mouldability of the hydrocolloid of Example 6. TABLE 2 shows also the greater penetration (21.5 mm) of the Example 6 adhesive by the stainless steel probe at the force of 4.5N, compared to that with the Eakin Cohesive product (18.0 mm). Because of the poor integrity of the Cohesive, its absorption could not be measured, as the adhesive melts into a soft, low viscosity gel. The other measured properties of the two adhesives are comparable.

TABLE 2

|  | Eakin Cohesive | Ex. 6 |
|---|---|---|
| Reverse tack, N/25 mm | 9.1 | 12.0 |
| Peel Adhesion 90° Teflon, N/25 mm | 2.6 | 4.8 |
| Shear Adhesion 0.5 kg, min | 18 | 20 |
| Thickness, mm | 2.60 | 2.45 |
| stat. Absorption, gm/sq. m/24 hr | Not Measurable | 7566 |
| Penetration/Softness, mm | 18.0 | 21.5 |
| Integrity, % | 10 | 98 |

The static absorption and the integrity of Example 6 in TABLE 2 differ slightly from the values shown for Example 6 in TABLE 1, because they were measured on a different batch of mouldable adhesive.

EXAMPLE 12

Figure 2:
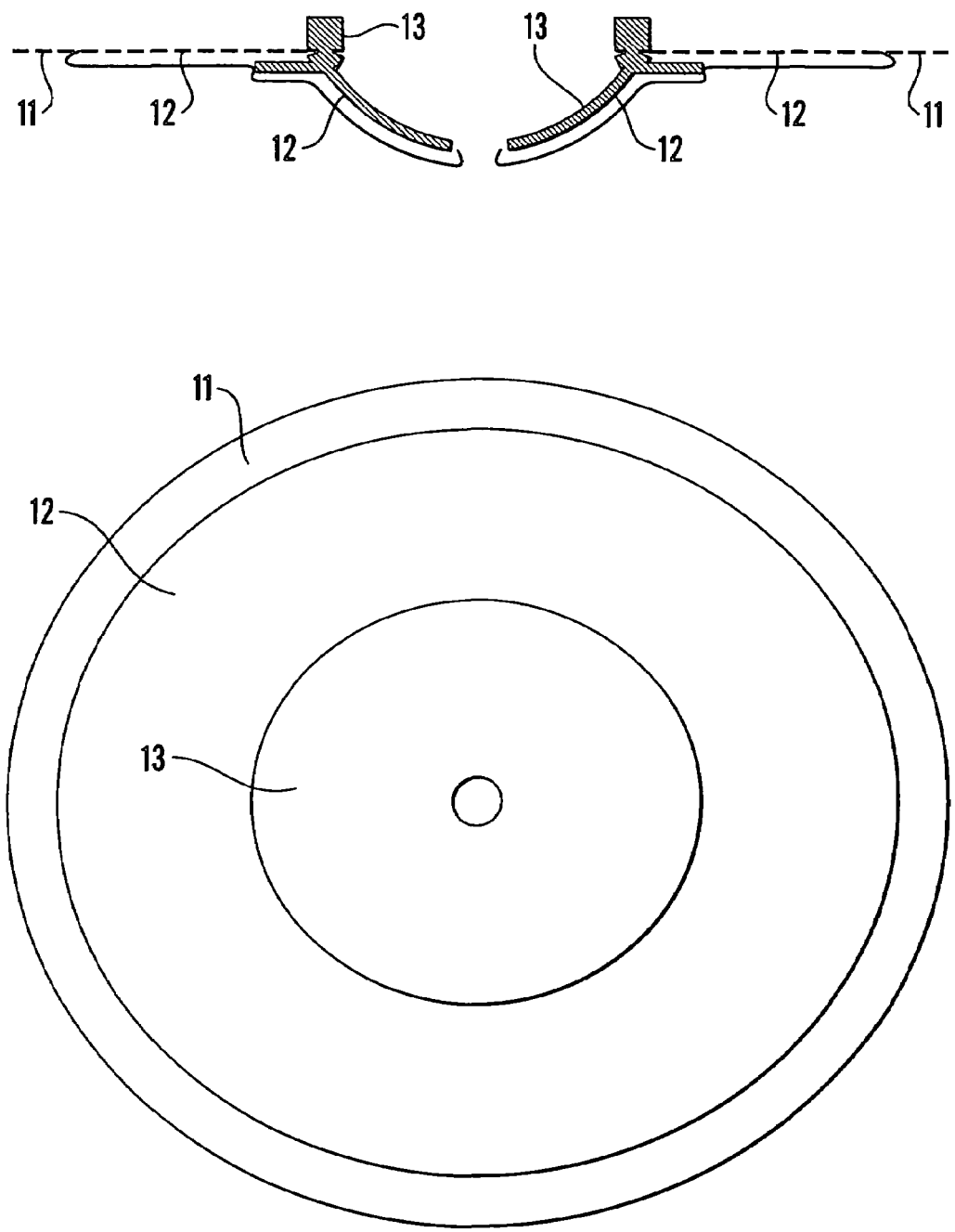
FIG. 2 is a schematic illustration of a convex body-side flange of a two-piece ostomy device, together with a cross-sectional view thereof.

The hydrocolloid from Example 6 is made into a convex body-side flange of a two piece ostomy-device, illustrated in FIG. 2. With reference to the FIG. 2, component 13 is an injection moulded body-side flange piece, with an integral flange circumferential to the outer edge of the convex form. The body-side flange is moulded from a blend of low molecular weight polyethylene and ethylene-vinyl acetate copolymer. Component 11 is an annular collar die cut from treated, waterproofed Sontara 8000 non-woven fabric which is coated with medical grade acrylic pressure sensitive adhesive on its underside, and is available as Lasso SA72 from Smith and Nephew, which can overlay the circumferential flange of the connector. Component 12 is the mouldable hydrocolloid adhesive, moulded to the underside of the convex flange and the non-woven overlay, using a matched die set which is heated to 100° C. in a 100 ton Bradley and Turton upstroking press. A vacuum moulded plastic protector, not shown in FIG. 2, with silicone release coating on its concave surface, can be made to fit on the underside of the construction to protect the adhesive until removal by the end-user.

EXAMPLES 13-27

Examples 13-27 show the formulation of mouldable hydrocolloids suitable for direct contact with wounds. The results are shown in TABLES 3 and 4. Generally, starch is not considered suitable for contact with wounds since it is likely to be a nutrient for any pathogenic organisms present. Aquasorb A500, crystalline sodium carboxymethyl cellulose available from Aqualon division of Hercules Chemical Company, generally was used as a replacement for the starch in these compositions. The formulations having the highest degree of integrity were integrated with a hot melt adhesive having a thermoplastic elastomer:liquid rubber ratio of 1:4. Examples 24-27 in comparison, with the same amount of hot melt adhesive but with a 1:1.5 ratio of thermoplastic elastomer:liquid rubber, were not found to have such high integrity. It was also found that the highest integrity products had, as the absorbent medium, blends of soluble and insoluble absorbents. Nevertheless, these compositions are also useful as mouldable hydrocolloid adhesives.

Example 23, when sterilised using gamma radiation at 25 KGy, showed excellent retention of integrity, and a moderate but still acceptable reduction in absorption capacity. The gel resulting from absorption of fluid is soft, will readily conform to the surface of a wound bed and will not cause significant pressure within the wound.

TABLE 3

|  | Formulation, wt % | | | | | | | |
|---|---|---|---|---|---|---|---|---|
|  | Ex. 13 | Ex. 14 | Ex. 15 | Ex. 16 | Ex. 17 | Ex. 18 | Ex. 19 | Ex. 20 |
| Hot Melt of Example | 1 | 1 | 1 | 1 | 1 | 1 | 1 | 1 |
| LVSI-101 | 6.61 | 7.94 | 6.61 | 6.61 | 4.76 | 4.71 | 6.53 | 4.76 |
| Kraton D-1161NS | 1.65 | 1.98 | 1.65 | 1.65 | 1.19 | 1.18 | 1.63 | 1.19 |
| Irganox 1010 | 0.07 | 0.08 | 0.07 | 0.07 | 0.05 | 0.05 | 0.07 | 0.05 |
| Vistanex LMMS | 34.17 | 35.00 | 35.00 | 35.00 | 35.00 | 34.57 | 34.57 | 35.00 |
| Pectin USP100 | — | — | 8.00 | 8.00 | 8.00 | 7.90 | 7.90 | 17.00 |
| Blanose 7H4XF | — | — | 20.00 | 20.00 | 20.00 | 19.75 | 19.75 | 32.00 |
| Aquasorb A500 | 49.16 | 45.00 | 17.00 | 18.67 | 17.00 | 20.74 | 16.79 | — |
| Parapol 1300 | 8.33 | 10.00 | 11.67 | 10.00 | 14.00 | 11.11 | 12.76 | 10.00 |
| Properties |  |  |  |  |  |  |  |  |
| Liquid rubber: Thermoplastic elastomer, wt/wt | 4.00 | 4.00 | 4.00 | 4.00 | 4.00 | 4.00 | 4.00 | 4.00 |
| Static Absorp Gms/sq. m./24 hrs | 11760 | 12027 | 7992 | 7810 | 7478 | 8214 | 7512 | 8518 |
| Integrity, % | 40 | 35 | 38 | 48 | 9 | 9 | 29 | 7 |
| Thickness, mm | 2.0 | 2.0 | 0.8 | 0.8 | 0.8 | 0.8 | 0.8 | 1.0 |

TABLE 4

| | Formulation, wt % | | | | | | | |
|---|---|---|---|---|---|---|---|---|
| | Ex. 21 | Ex. 22 | Ex. 23 Non-sterile | Ex. 23 sterile | Ex. 24 | EX. 25 | Ex. 26 | Ex. 27 |
| Hot Melt of Example | 1 | 1 | 1 | 1 | 2 | 2 | 2 | 2 |
| LVSI-101 | 6.61 | 7.94 | 7.94 | 7.94 | 5.95 | 5.95 | 5.95 | 5.95 |
| Kraton D-1161NS | 1.65 | 1.98 | 1.98 | 1.98 | 3.97 | 3.97 | 3.97 | 3.97 |
| Irganox 1010 | 0.07 | 0.08 | 0.08 | 0.08 | 0.08 | 0.08 | 0.08 | 0.08 |
| Vistanex LMMS | 35.00 | 35.00 | 35.00 | 35.00 | 35.00 | 35.00 | 30.00 | 32.50 |
| Pectin USP100 | 15.00 | 15.00 | 8.00 | 8.00 | — | 8.00 | — | 8.00 |
| Blanose 7H4XF | 30.00 | 30.00 | 20.00 | 20.00 | — | 20.00 | — | 20.00 |
| Aquasorb A500 | 1.67 | — | 17.00 | 17.00 | 45.00 | 17.00 | 45.00 | 17.00 |
| Parapol 1300 | 10.00 | 10.00 | 10.00 | 10.00 | 10.00 | 10.00 | 15.00 | 12.50 |
| Properties | | | | | | | | |
| Liquid rubber: Thermoplastic elastomer, wt/wt | 4.00 | 4.00 | 4.00 | 4.00 | 1.50 | 1.50 | 1.50 | 1.50 |
| Static Absorp Gms/sq. m./24 hrs | 7562 | 7819 | 9006 | 6547 | 11865 | 9802 | 11254 | 7806 |
| Integrity, % | 59 | 70 | 78 | 74 | 10 | 10 | 10 | 10 |
| Thickness, mm | 2.0 | 2.0 | 2.0 | 2.0 | 2.0 | 2.0 | 2.0 | 2.0 |

The invention claimed is:

1. A convex body-side flange of an ostomy device, having formed thereon a layer of a mouldable, pressure-sensitive, hydrocolloid adhesive composition comprising
   a continuous phase of a mixture of (a) a thermoplastic elastomer, present in an amount of 1-5 wt. % of the composition, (b) a liquid rubber, wherein the weight ratio of thermoplastic elastomer to liquid rubber is 1:0.5 to 1:7, (c) polyisobutylene having a viscosity-average molecular weight of from 35,000-70,000, present in an amount of from 25-45 wt. % of the composition, (d) a low molecular weight liquid polybutene, present in an amount of from 5-20 wt. % of the composition; and
   a discontinuous phase of one or more water-soluble and/or water swellable absorbent polymers.

2. A convex body-side flange of an ostomy device according to claim 1, wherein the liquid rubber has a molecular weight of 25,000 to 50,000.

3. A convex body-side flange of an ostomy device according to claim 1, wherein the low molecular weight polybutene has a molecular weight of 1,000 to 3,000 according to ASTM D445.

4. A convex body-side flange of an ostomy device according to claim 1, wherein the content of thermoplastic elastomer, based on the total composition, is not more than 3 wt. %.

5. A convex body-side flange of an ostomy device according to claim 4 wherein the content of thermoplastic elastomer does not exceed 2 wt. %.

6. A convex body-side flange of an ostomy device according to claim 1, wherein the content of liquid rubber does not exceed 10 wt. % of the composition.

7. A convex body-side flange of an ostomy device according to claim 1 wherein the polyisobutylene comprises from 30-40 wt. % of the composition.

8. A convex body-side flange of an ostomy device according to claim 1, wherein the low molecular weight polybutene comprises from 7-15 wt. % of the composition.

9. A convex body-side flange of an ostomy device according to claim 1, wherein the discontinuous phase comprises not more than 60 wt. % of the total composition.

\* \* \* \* \*